United States Patent [19]
Gall

[11] 3,941,803
[45] Mar. 2, 1976

[54] 2-(IMIDAZOL-1-YL)BENZOPHENONES
[75] Inventor: Martin Gall, Kalamazoo, Mich.
[73] Assignee: The Upjohn Company, Kalamazoo, Mich.
[22] Filed: Mar. 28, 1975
[21] Appl. No.: 563,079

[52] U.S. Cl............ 260/309; 260/566 B; 260/578; 260/999
[51] Int. Cl.[2]............... C07D 233/60; C07D 209/48
[58] Field of Search....:........................... 260/309

[56] References Cited
UNITED STATES PATENTS
3,534,061 10/1970 Black ................................. 260/309
3,763,179 10/1973 Gall .................................... 260/309

Primary Examiner—Natalie Trousof
Attorney, Agent, or Firm—Hans L. Berneis

[57] ABSTRACT

Compounds of formula II

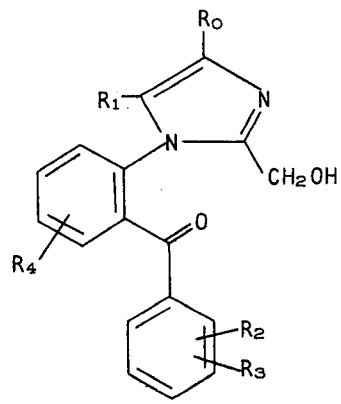

and its phthalimide derivative III:

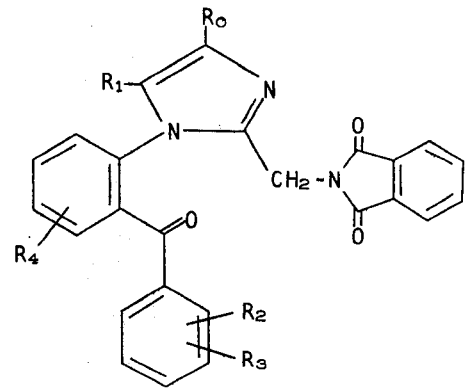

wherein $R_0$ and $R_1$ are hydrogen or alkyl of 1 to 3 carbon atoms, inclusive; wherein $R_2$ is hydrogen, chloro, fluoro, or trifluoromethyl; wherein $R_3$ is hydrogen, or fluoro with the proviso that $R_3$ is not fluoro, if $R_2$ is chloro or trifluoromethyl; and wherein $R_4$ is hydrogen, fluoro, chloro, bromo, nitro, or trifluoromethyl are prepared by reacting a compound of formula I:

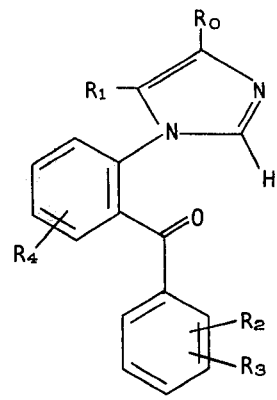

wherein $R_0$, $R_1$, $R_2$, $R_3$, and $R_4$ are defined as above, with formaldehyde to produce compound II and reacting II with phthalimide, triphenylphosphine and finally diethyl azodicarboxylate to give compound III.

Compounds II and III are useful as important intermediates for the production of known 6-phenyl-4H-imidazo[1,2-a][1,4]benzodiazepine which compounds are active as tranquilizers and antianxiety agents.

22 Claims, No Drawings

2-(IMIDAZOL-1-YL)BENZOPHENONES

BACKGROUND OF THE INVENTION

1. Field of the Invention

This invention is directed to new organic compounds and more specifically to 2-[2-(hydroxymethyl)imidazo-1-yl]benzophenones and 2-[2-(phthalimidomethyl)imidazo-1-yl]benzophenones and a process therefor.

The novel compound and the process of production therefor can be illustratively represented as follows:

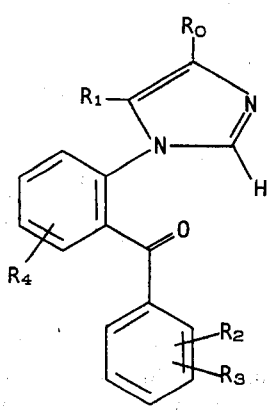

I

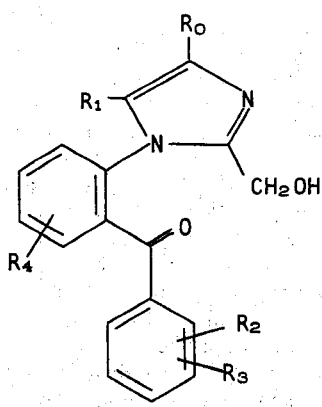

II

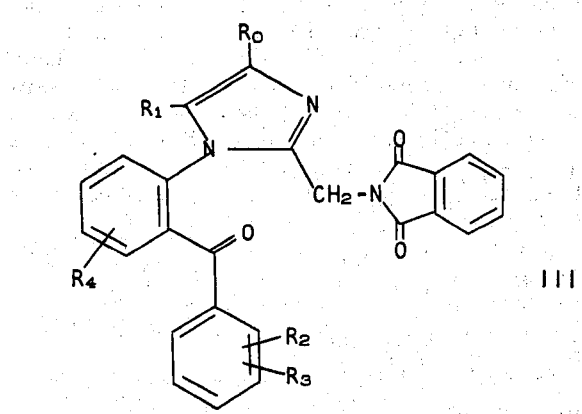

III wherein $R_0$ and $R_1$ are hydrogen or alkyl of 1 to 3 carbon atoms, inclusive; wherein $R_2$ is hydrogen, chloro, fluoro, or trifluoromethyl; wherein $R_3$ is hydrogen, or fluoro with the proviso that $R_3$ is not fluoro, if $R_2$ is chloro or trifluoromethyl; and wherein $R_4$ is hydrogen, fluoro, chloro, bromo, nitro, or trifluoromethyl.

The process of this invention comprises: heating a compound of formula I with aqueous formalin with or without an organic inert solvent or paraformaldehyde in toluene or xylene or diglyme to a temperature between 100° to 160° C. to obtain the corresponding compound II; and treating II with triphenylphosphine, phthalimide and finally diethyl azodicarboxylate at −10° to 15° C. in an inert organic solvent such as tetrahydrofuran to give the corresponding compound III.

2. Description of the Preferred Embodiment

Alkyl groups of 1 to 3 carbon atoms inclusive are methyl, ethyl, propyl, and isopropyl.

The more preferred compounds II of this invention have the specific formula IIA:

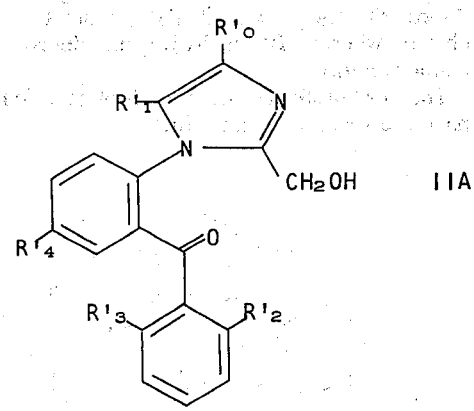

IIA wherein $R'_0$ and $R'_1$ are hydrogen or methyl; wherein $R'_2$ is hydrogen, chloro, or fluoro; wherein $R'_3$ is hydrogen, or fluoro with the proviso that $R'_3$ is not fluoro if $R'_2$ is chloro; wherein $R'_4$ is hydrogen, chloro, fluoro, or trifluoromethyl.

The most preferred compounds II of this invention have the specific formula IIB:

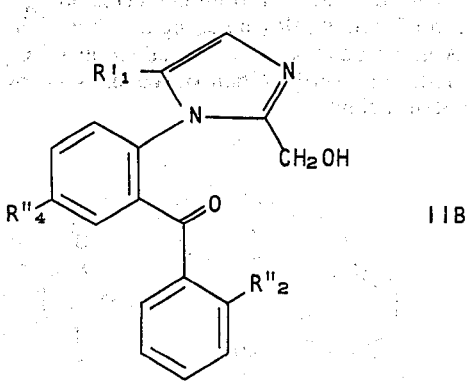

IIB wherein $R'_1$ is hydrogen or methyl; wherein $R''_2$ is hydrogen or chloro; wherein $R''_4$ is hydrogen, chloro, or fluoro.

The more preferred compounds III have the specific formula IIIA

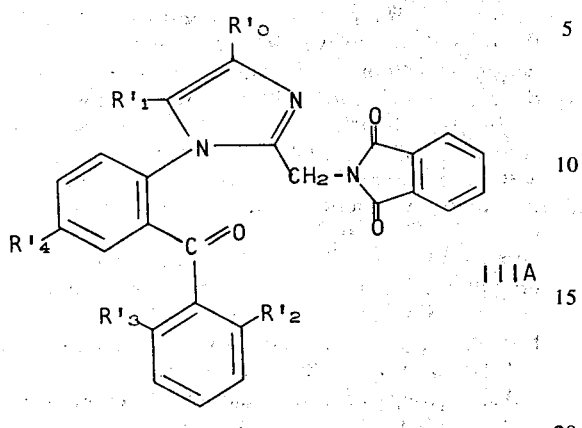

wherein R'₁ is hydrogen or methyl; wherein R'₂ is hydrogen, chloro, or fluoro; wherein R'₃ is hydrogen or fluoro with the proviso that R'₃ is not fluoro if R'₂ is chloro; wherein R'₄ is hydrogen, chloro, fluoro, or trifluoromethyl.

The most preferred compounds of generic formula III have the specific formula IIIB

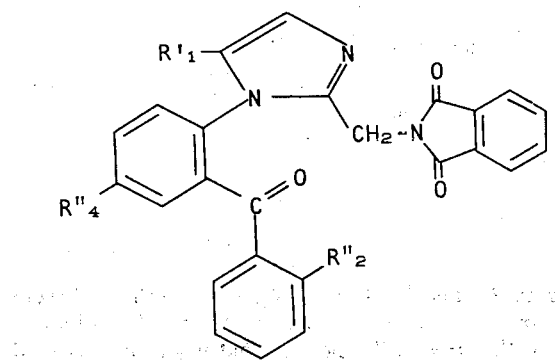

wherein R'₁ is hydrogen or methyl; wherein R"₂ is hydrogen or chloro; wherein R"₄ is hydrogen, chloro, or fluoro.

The compound of formulae II (including IIA and IIB) and of formula III (including IIIA and IIIB) are useful as intermediates for the production of 6-phenyl-4H-imidazo-[1,2-a][1,4]benzodiazepines IV by a scheme shown below:

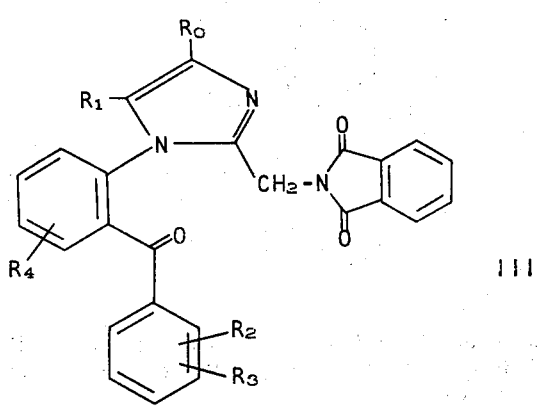

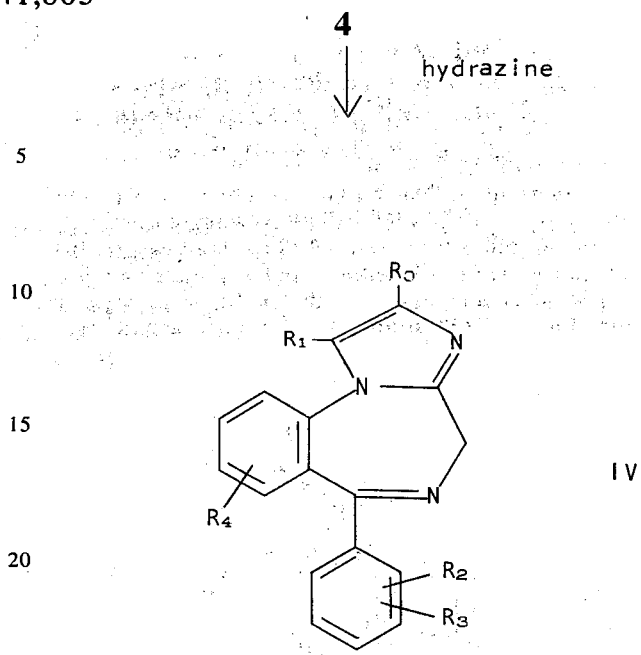

The activity of compounds of formula IV as tranquilizers sedatives and muscle relaxants is discussed in Belgian Patent No. 768,781, granted Feb. 5, 1973 or in South African Patent No. 72/4880 sealed October 1973.

The imidazobenzophenones of formula I are prepared as shown in the preparations.

In carrying out the process of this invention a selected starting compound of formula I is reacted with paraformaldehyde in a suitable inert organic solvent e.g. xylene, toluene, diglyme, or with an aqueous solution of formaldehyde such as commercial 37% aqueous formaldehyde (formalin) in a bomb at 1–20 atmosphere at 100° to 170° C. during a period of 1–12 hours. Thereafter the reaction mixture is quenched in an aqueous base e.g. sodium, potassium or barium hydroxide or sodium or potassium carbonate or bicarbonate and the product II is isolated and purified by conventional procedures e.g. extraction, chromatography, crystallization, and the like.

Compound II is then treated in a suspension of an inert organic solvent with phthalimide and triphenylphosphine. The inert solvent is usually tetrahydrofuran, monoglyme, diglyme or triglyme. In the preferred embodiment of this invention the phthalimide and triphenylphosphine are used in excess of 5–25% above the mol equivalent of compound II and the reaction is carried out between −10° to 15° C. during ½ to 2 hours. Thereafter, at a temperature of 0° to 5° C. the reaction mixture is treated dropwise with diethyl azodicarboxylate using the equimolar amount in which the phthalimide above was used. The addition is carried out under continuous stirring during ½ to 2 hours and thereafter the stirring is continued for 8–24 hours permitting the solution to warm to room temperature (20°–30° C.). After this period the reaction is terminated and the product III, thus obtained, is isolated and purified by conventional means such as extraction, filtration, chromatography and/or crystallization.

The following preparations and examples are illustrative of the processes and products of the present invention, but are not to be construed as limiting.

Preparation 1 — 2-Amino-5-chlorobenzophenone hydrazine

A mixture of 27.2 g. (0.117 mol) of 2-amino-5-chlorobenzophenone in 170 ml. of diethylene glycol and 23 ml. (0.45 mol) of 99% hydrazine hydrate is kept at reflux for a total of 7 hours. The solution is allowed to cool overnight to room temperature. The solid which results is mixed with 400 ml. of water and extracted into benzene; the layers are separated and the benzene portion dried over anhydrous magnesium sulfate and concentrated. Crystallization of te residue from ether/hexane gives 13.5 g. (46.8%) of 2-amino-5-chlorobenzophenone hydrazone of melting point 133°–133.5° C.

Anal. calcd. for $C_{13}H_{12}ClN_3$: C, 63.55; H, 4.93; N, 17.11; Cl, 14.43. Found: C, 63.58; H, 4.95; N, 17.32; Cl, 14.39.

Preparation 2 — 2-Amino-2',5-dichlorobenzophenone hydrazone

In the manner given in Preparation 1, 2-amino-2',5-dichlorobenzophenone is refluxed with hydrazine hydrate in diethylene glycol to give 2-amino-2',5-dichlorobenzophenone hydrazine.

Preparation 3 —
2-Amino-5-chloro-2',6'-difluorobenzophenone hydrazone

In the manner given in Preparation 1, 2-amino-5-chloro-2',6'-difluorobenzophenone is refluxed with hydrazine hydrate in diethylene glycol to give 2-amino-5-chloro-2',6'-difluorobenzophenone hydrazone.

Preparation 4 —
2-Amino-2'-chloro-5-nitrobenzophenone hydrazone

In the manner given in Preparation 1, 2-amino-2'-chloro-5-nitrobenzophenone is refluxed with hydrazine hydrate in diethylene glycol to give 2-amino-2'-chloro-5-nitrobenzophenone hydrazone.

Preparation 5 — 2-Amino-benzophenone hydrazone

In the manner given in Preparation 1, 2-aminobenzophenone is refluxed with hydrazine hydrate in diethylene glycol to give 2-aminobenzophenone hydrazone.

Preparation 6 — 2-Amino-2'-chlorobenzophenone hydrazone

In the manner given in Preparation 1, 2-amino-2'-chlorobenzophenone is refluxed with hydrazine hydrate in diethylene glycol to give 2-amino-2'-chlorobenzophenone hydrazone.

Preparation 7 — 5-Fluoro-2-aminobenzophenone hydrazone

In the manner given in Preparation 1, 5-fluoro-2-aminobenzophenone is refluxed with hydrazine hydrate in diethylene glycol to give 5-fluoro-2-aminobenzophenone hydrazone.

Preparation 8 —
2-Amino-5-chloro-2'-fluorobenzophenone hydrazone

In the manner given in Preparation 1, 2-amino-5-chloro-2'-fluorobenzophenone is refluxed with hydrazine hydrate in diethylene glycol to give 2-amino-5-chloro-2'-fluorobenzophenone hydrazone.

Preparation 9 —
5-(Trifluoromethyl)-2-amino-benzophenone hydrazone

In the manner given in Preparation 1, 5-(trifluoromethyl)-2-aminobenzophenone is refluxed with hydrazine hydrate in diethylene glycol to give 5-(trifluoromethyl)-2-aminobenzophenone hydrazone.

Preparation 10 — 2-Amino-5-nitrobenzophenone hydrazone

In the manner given in Preparation 1, 2-amino-5-nitrobenzophenone is refluxed with hydrazine hydrate in diethylene glycol to give 2-amino-5-nitrobenzophenone hydrazone.

In the same manner given in preparations 1 through 10 other 2-aminobenzophenone hydrazones can be synthesized. Representative compounds thus produced include:

2-amino-2'-chloro-5-(trifluoromethyl)-benzophenone hydrazone;
2-amino-5-bromo-2'-fluorobenzophenone hydrazone;
2-amino-5-fluoro-2'-chlorobenzophenone hydrazone;
2-amino-5-bromo-2'-chlorobenzophenone hydrazone;
2-amino-3',5-dichlorobenzophenone hydrazone;
2-amino-4-chlorobenzophenone hydrazone;
2-amino-3-(trifluoromethyl)benzophenone hydrazone;
2-amino-3'-chlorobenzophenone hydrazone;
2-amino-4',5-dichlorobenzophenone hydrazone;
2-amino-5-bromo-3'-chlorobenzophenone hydrazone;
2-amino-5-bromobenzophenone hydrazone;
2-amino-3-chloro-2'-fluorobenzophenone hydrazone;
2-amino-4-nitrobenzophenone hydrazone;
2-amino-2'-fluoro-5-(trifluoromethyl)benzophenone hydrazone;
2-amino-4-bromo-2'-chlorobenzophenone hydrazone; and the like.

Preparation 11 — 2-benzyl-4-chloroaniline

Potassium hydroxide pellets (16.1 g., 245 mmol) are gound and dissolved in 85 ml. of refluxing diethylene glycol. Volatile materials are distilled until the temperature of the liquid reaches 200° C. The solution is then cooled to room temperature and 13.5 g. (54.6 mmol) of 2-amino-5-chlorobenzophenone hydrazone is added, while the syrupy liquid is gently reheated. At 100° C. all the hydrazone has dissolved. The temperature is maintained between 120°–150° C. for 45 minutes until gas evolution ceases. After a total heating period of 1.5 hours the solution is cooled, poured onto ice and extracted with benzene. The benzene layer is separated, dried over anhydrous magnesium sulfate and concentrated to yield an orange oil. Distillation affords 9.9 g. of 2-benzyl-4-chloroaniline (89.2%) yellow oil of boiling point 125°–140° C. (at 0.1 mm Hg).

Anal. calcd. for $C_{13}H_{12}ClN$: C, 71.72; H, 5.56; N, 6.44; Cl, 16.28. Found: C, 71.55; H, 5.51; N, 6.58; Cl, 16.16.

Preparation 12 — 2-(o-chlorobenzyl)-4-chloroaniline

In the manner given in Preparation 11, 2-amino-2',5-dichlorobenzophenone hydrazone is refluxed with potassium hydroxide in diethylene glycol to give 2-(o-chlorobenzyl)-4-chloroaniline, boiling point 140°–148° (0.15 mm Hg), melting point 64°–65° C.

Anal. calcd. for $C_{13}H_{11}Cl_2N$: C, 61.92; H, 4.40; N, 5.56; Cl, 28.12; Found: C, 62.00; H, 4.46; N, 5.61; Cl, 28.28.

Preparation 13 —
4-Chloro-α-(2,6-difluorophenyl)-o-toluidine

In the manner given in Preparation 11, 2-amino-5-chloro-2',6'-difluorobenzophenone hydrazone is refluxed with potassium hydroxide in diethylene glycol to give 4-chloro-α-(2,6-difluorophenyl)-o-toluidine.

Preparation 14 — 2-(o-chlorobenzyl)-4-nitroaniline

In the manner given in Preparation 11, 2-amino-2'-chloro-5-nitrobenzophenone hydrazone is refluxed with potassium hydroxide in diethylene glycol to give 2-(o-chlorobenzyl)-4-nitroaniline.

Preparation 15 — 2-Benzylaniline

In the manner given in Preparation 11, 2-aminobenzophenone hydrazone is refluxed with potassium hydroxide in diethylene glycol to give 2-benzylaniline.

Preparation 16 — 2-(o-chlorobenzyl)aniline

In the manner given in Preparation 11, 2-amino-2'-chlorobenzophenone hydrazone is refluxed with potassium hydroxide in diethylene glycol to give 2-(o-chlorobenzyl)aniline.

Preparation 17 — 4-Fluoro-α-phenyl-o-toluidine

In the manner given in Preparation 11, 2-amino-5-fluorobenzophenone hydrazone is refluxed with potassium hydroxide in diethylene glycol to give 4-fluoro-α-phenyl-o-toluidine.

Preparation 18 — 2-(o-fluorobenzyl)-4-chloroaniline

In the manner given in Preparation 11, 2-amino-2'-fluoro-5-chlorobenzophenone hydrazone is refluxed with potassium hydroxide in diethylene glycol to give 2-(o-fluorobenzyl)-4-chloroaniline.

Preparation 19 —
4-(Trifluoromethyl)-α-phenyl-o-toluidine

In the manner given in Preparation 11, 2-amino-5-(trifluoromethyl)benzophenone is refluxed with potassium hydroxide in diethylene glycol to give 4-(trifluoromethyl)-α-phenyl-o-toluidine.

Preparation 20 — 2-Benzyl-4-nitroaniline

In the manner given in Preparation 11, 2-amino-5-nitrobenzophenone hydrazone is refluxed with potassium hydroxide in diethylene glycol to give 2-benzyl-4-nitroaniline.

In the manner given in the preceding preparations other α-phenyl-o-toluidines can be synthesized. Representative compounds thus obtained include:
2-(o-chlorobenzyl)-5-bromoaniline;
2-(o-chlorobenzyl)-4-(trifluoromethyl)aniline;
4-chloro-α-(m-chlorophenyl)-o-toluidine;
4-bromo-α-(o-chlorophenyl-o-toluidine;
5-bromo-α-(o-fluorophenyl)-o-toluidine;
α-(o-fluorophenyl)-o-toluidine;
4-bromo-α-phenyl-o-toluidine;
3-fluoro-α-(o-fluorophenyl)-o-toluidine;
4-fluoro-α-(o-chlorophenyl)-o-toluidine;
3-(trifluoromethyl)-α-phenyl-o-toluidine; and the like.

Preparation 21 —
1-(4-chloro-α-phenyl-o-tolyl)imidazole

A. A solution of 50.6 g. (0.233 mmol) of 2-benzyl-4-chloroaniline and 82.85 g. (0.5095 mole) of triethyl orthoformate are kept at reflux during 5 hours. About 75 ml. of ethanol and other low boiling materials are distilled leaving an oily residue.

B. The residual oil is then cooled to room temperature, dissolved in 500 ml. of methanol and treated with 83.5 g. (0.795 mol) of aminoacetaldehyde, dimethyl acetal. The solution is refluxed for 3 hours until the imino ether has reacted completely.

C. The solvent is then removed in vacuo to give an oil which is dissolved in 1 liter of monoglyme. To this solution is carefully added 34.9 ml. of titanium tetrachloride (60.4 g., 0.318 mol). The solution turns brown immediately and warms considerably during the addition of the metal salt. The reaction mixture is stirred at ambient temperature for 10 minutes, then refluxed for 4 hours. The reaction mixture is permitted to cool overnight, then worked up by pouring into 5.0 liter of cold 5% aqueous sodium hydroxide solution and extracted with chloroform (approximately 9 liter of solvent is used). The organic layers re combined, washed with saturated aqueous sodium chloride, dried over anhydrous magnesium sulfate and concentrated to a syrup to give 51.6 g. of a black tarry substance. This is chromatographed over 2500 g. of silica gel and eluted wit ethyl acetate, taking 1-liter fractions. The product is isolated in fractions 8 to 14 to give, after recrystallization from ether/hexane, 29.77 g. (48%) of 1-(4-chloro-α-phenyl-o-tolyl)imidazole of melting point 69°–70.5° C.

Anal. calcd. for $C_{16}H_{13}ClN_2$; mw. 268.73: c, 71.51; H, 4.87; N, 10.43; Cl, 13.19. Found: C, 71.81; H, 4.82; N, 10.42; Cl, 13.31.

Preparation 22 —
1-[4-Chloro-α-(o-chlorophenyl)-o-tolyl]imidazole

A. 4-Chloro-α-(o-chlorophenyl)-o-toluidine (58.7 g., 0.233 mol) is refluxed for 3 hours with 83.0 g. (0.509 mol) of triethyl orthoformate to remove ethanol leaving an oily residue.

B. This residue is cooled to room temperature, dissolved in 500 ml. of methanol and treated with 83.5 g. (0.795 mol) of aminoacetaldehyde, dimethylacetal. The solution is stirred at room temperature for 20 minutes and then refluxed for 3½ hours.

C. The solvent is removed in vacuo and the resulting oil, dissolved in 1 l. of monoglyme, is treated cautiously with 34.9 ml. (60.4 g., 0.318 mol) of titanium tetrachloride. The reaction mixture is stirred at ambient temperature for 10 minutes, then refluxed for 4 hours, cooled to room temperature, poured onto ice and neutralized with 5.0 l. of cold 10% aqueous sodium hydroxide solution. The mixture is treated with chloroform and both layers are filtered through Celite (activated carbon) to remove suspended solids. The layers are separated and the aqueous layer is extracted thoroughly with methylene chloride. The combined organic extracts are washed with brine, dried over anhydrous magnesium sulfate and concentrated in vacuo to an oil (140.0 g. (which is chromatographed over 4.8 kg. of silica gel by eluting with 30% ethyl acetate/70% Skellysolve B hexanes mixtures and taking 600 ml. fractions. After the 20th fraction the column is eluted with a 50% ethyl acetate/Skellysolve B hexane mixture. The product is isolated in fractions 21–29 and crystallized from ethyl acetate to afford 18.43 g. 1-[4-chloro-α-(o-chlorophenyl)-o-tolyl]imidazole of melting point 62°–63° C. An analytical sample has a melting point 63.5°–64.5° C.

Anal. calcd. for $C_{16}H_{12}Cl_2N_2$, mw 303.19: C, 63.38; H, 3.99; N, 9.24; Cl, 23.39. Found: C, 63.15; H, 3.94; N, 9.19; Cl, 23.18.

Preparation 23 —
5-Methyl-1-(4-chloro-α-phenyl-o-tolyl)imidazole

A. A solution of 5.06 g. (23.3 mmol) of 2-benzyl-4-chloroaniline and 8.28 g. (51.0 mol) of triethyl orthoformate is refluxed for five hours, and the ethanol distilled. The resulting yellow oil is dissolved in 25 ml. of absolute ethanol, treated with 2-methyl-2-(aminomethyl)-1,3-dioxolane and heated for 1.5 hours at reflux. All the volatile liquids are removed in vacuo to afford 5.26 g. of solid which is filtered and washed with hexane. The analytical sample recrystallizes from ethyl acetate/hexane and has a melting point 105°–107° C.

Anal. calcd. for $C_{19}H_{21}ClN_2O_2$, mw 344.83: C, 66.17; H, 6.14; N, 8.13; cl, 10.28. Found: C, 65.98; H, 6.12; N, 8.03; Cl, 10.35.

B. 5-Methyl-1-(4-chloro-α-phenyl-o-tolyl(imidazole

The product obtained from A (2.77 g., 8.11 mole) is dissolved in 40 ml. of monoglyme and treated carefully at room temperature with 1.22 ml. (2.10 g., 11.1 mmol) of reagent titanium tetrachloride. After the initial vigorous exothermic reaction has subsided, the reaction mixture is heated to reflux on a steam bath for 3 hours. The reaction mixture is quenched on ice, neutralized, extracted with chloroform, dried and chromatographed over 150 g. of silica gel by eluting with 100 ml. of ethyl acetate and 900 ml. of a 1/99 methanol/ethyl acetate mixture (18 ml. fractions are collected). The product is collected in fractions 24-37 and crystallized from ethyl acetate/hexane mixtures, to afford 0.71 g. of 5-methyl-1-(4-chloro-α-phenyl-o-tolyl)imidazole of melting point 64°–66° C. A second crop weighs 0.17 g. The analytical sample, crystallizes from ethyl acetate/hexane mixtures and has a melting point of 65°–66° C.

Anal. calcd. for $C_{17}H_{15}ClN_2$: C, 72.21; H, 5.35; N, 9.91; Cl, 12.54. Found: C, 71.97; H, 5.38; N, 9.79; Cl, 12.85.

Preparation 24 —
1-[4-Nitro-α-(o-chlorophenyl)-o-tolyl]imidazole

In the manner given in Preparation 21, 4-nitro-α-(o-chlorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-nitro-α-(o-chlorophenyl)-o-tolyl]imidazole.

Preparation 25 —
5-Methyl-1-(4-nitro-α-(o-chlorophenyl)-o-tolyl-)imidazole In the manner given in Preparation 23, 4-nitro-α-(o-chlorophenyl)-o-toluidine is reacted with triethyl orthoformate. The resulting oil is heated with 2-methyl-2-(aminomethy)-1,3-dioxolane, and the resulting product treated with titanium tetrachloride to give 5-methyl-1-(4-nitro-α-(o-chlorophenyl-o-tolyl)imidazole.

Preparation 26 —
1-[4-Fluoro-α-(o-chlorophenyl)-o-tolyl]imidazole

In the manner given in Preparation 21, 4-fluoro-α-(o-chlorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-fluoro-α-(o-chlorophenyl)-o-tolyl]imidazole.

Preparation 27 —
5-Ethyl-1-[4-fluoro-α-(o-chlorophenyl)-o-tolyl-]imidazole In the manner given in Preparation 23, 4-fluoro-α-(o-chlorophenyl)-o-toluidine is reacted with triethyl orthoformate, the resulting oil is heated with 2-ethyl-2-(aminomethyl)-1,3-dioxolane, and the resulting product treated with titanium tetrachloride to give 5-ethyl-1-[4-fluoro-α-(o-chlorophenyl)-o-tolyl]imidazole.

Preparation 28 —
1-[4-(trifluoromethyl)-α-phenyl-o-tolyl]imidazole

In the manner given in Preparation 21, 4-(trifluoromethyl)-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-(trifluoromethyl)-α-phenyl-o-tolyl]imidazole.

Preparation 29 —
5-Methyl-1-[4-(trifluoromethyl)-α-phenyl-o-tolyl-]imidazole In the manner given in Preparation 23, 4-(trifluoromethyl)-α-phenyl-o-toluidine is reacted with triethyl orthoformate, the resulting oil is heated with 2-methyl-2-(aminomethyl)-1,3-dioxolane, and the resulting product treated with titanium tetrachloride to give 5-methyl-1-[4-(trifluoromethyl)-o-phenyl-o-tolyl]imidazole.

Preparation 30 —
1-[4-Chloro-α-(2,6-difluorophenyl)-o-tolyl]imidazole

In the manner given in Preparation 21, 4-chloro-α-(2,6-difluorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-chloro-α-(2,6-difluorophenyl)-o-tolyl]imidazole.

Preparation 31 —
4-Ethyl-5-methyl-1-[4-chloro-α-(2,6-difluorophenyl)-o-tolyl]imidazole In the manner given in Preparation 23, 4-chloro-α-(2,6-difluorophenyl)-o-toluidine is reacted with triethyl orthoformate, the resulting oil is heated with 2-ethyl-2-(1-aminoethyl)-1,3-dioxolane, and the resulting product treated with titanium tetrachloride to give 4-ethyl-5-methyl-1-[4-chloro-α-(2,6-difluorophenyl)-o-tolyl]imidazole.

Preparation 32 —
1-(4-Nitro-α-phenyl-o-tolyl)imidazole

In the manner given in Preparation 21, 4-nitro-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-(4-nitro-α-phenyl-o-tolyl)imidazole.

Preparation 33 —
5-Methyl-1-(4-nitro-α-phenyl-o-tolyl)imidazole

In the manner given in Preparation 23, 4-nitro-α-phenyl-o-toluidine is reacted with triethyl orthoformate the resulting oil is heated with 2-methyl-2-(aminomethyl)-1,3-dioxolane, and the resulting product treated with titanium tetrachloride to give 5-methyl-1-(4-nitro-α-phenyl-o-tolyl)imidazole.

Preparation 34 —
1-(4-fluoro-α-phenyl-o-tolyl)imidazole

In the manner given in Preparation 21, 4-fluoro-α-phenyl-o-toluidine is reacted first with trimethyl orthoformate; the resulting product is reacted with aminoacetaldehyde, dimethyl acetal, and the resulting product of this reaction is heated with titanium tetrachloride in monoglyme to give 1-(4-fluoro-α-phenyl-o-tolyl)imidazole.

Preparation 35 —
5-Methyl-1-[4-chloro-α-(o-chlorophenyl)-o-tolyl]imidazole

In the manner given in Preparation 21, 4-chloro-α-(o-chlorophenyl)-o-toluidine is reacted with triethyl orthoformate, the resulting oil is heated with 2-methyl-2-(aminomethyl)-1,3-dioxolane, and the resulting product treated with titanium tetrachloride to give 5-methyl-1-[4-chloro-α-(o-chlorophenyl)-o-tolyl]imidazole.

Preparation 36 — 1-(α-phenyl-o-tolyl)imidazole

In the manner given in Preparation 21, α-phenyl-o-toluidine is reacted first with trimethyl orthoformate, the resulting product is reacted with aminoacetaldehyde, dimethyl acetal, and the resulting product of this reaction is heated with titanium tetrachloride in monoglyme to give 1-(α-phenyl-o-tolyl)imidazole.

Preparation 37 —
5-Methyl-1-(α-phenyl-o-tolyl)imidazole

In the manner given in Preparation 23, α-phenyl-o-toluidine is reacted with triethyl orthoformate, the resulting oil is heated with 2-methyl-2-(aminomethyl)-1,3-dioxolane, and the resulting product treated with titanium tetrachloride to give 5-methyl-1-(α-phenyl-o-tolyl)imidazole.

Preparation 38 —
1-[4-Chloro-α-(o-fluorophenyl)-o-tolyl]imidazole

In the manner given in Preparation 21, 4-chloro-α-(o-fluorophenyl)-o-toluidine is reacted first with trimethyl orthoformate; the resulting product is reacted with aminoacetaldehyde, dimethyl acetal, and the resulting product of this reaction is heated with titanium tetrachloride in monoglyme to give 1-[4-chloro-α-(o-fluorophenyl)-o-tolyl]imidazole.

Preparation 39 —
5-Methyl-1-[α-(o-chlorophenyl)-o-tolyl]imidazole

In the manner given in Preparation 23, α-(o-chlorophenyl)-o-toluidine is reacted with triethyl orthoformate, the resulting oil is heated with 2-methyl-2-(aminomethyl)-1,3-dioxolane, and the resulting product treated with totanium tetrachloride to give 5-methyl-1-[α-(o-chlorophenyl)-o-tolyl]imidazole.

Preparation 40 —
4,5-Diethyl-1-[α-(o-fluorophenyl)-o-tolyl]imidazole

In the manner given in Preparation 23, α-(o-fluorophenyl)-o-toluidine is reacted with triethyl orthoformate, the resulting oil is heated with 2-ethyl-2-(1-aminoethyl)-1,3-dioxolane, and the resulting product treated with titanium tetrachloride to give 4,5-diethyl-1-[α-(o-fluorophenyl)-o-tolyl]imidazole.

Preparation 41 —
1-[4-bromo-α-(o-chlorophenyl)-o-tolyl]-imidazole

In the manner given in Preparation 21, 4-bromo-α-(o-chlorophenyl)-o-toluidine is reacted first with trimethyl orthoformate; the resulting product is reacted with aminoacetaldehyde, dimethyl acetal and the resulting product of this reaction is heated with titanium tetrachloride in monoglyme to give 1-[4-bromo-α-(o-bromophenyl)-o-tolyl]imidazole.

Preparation 42 —
5-Propyl-1-[4-bromo-α-(o-chlorophenyl)-o-tolyl]imidazole

In the manner given Preparation 23, 4-bromo-α-(o-chlorophenyl)-o-toluidine is reacted with triethyl orthoformate, the resulting oil is heated with 2-propyl-2-(aminomethyl)-1,3-dioxolane, and the resulting product treated with titanium tetrachloride to give 5-propyl-1-[4-bromo-α-(o-chlorophenyl)-o-tolyl]imidazole.

Preparation 43 —
4-Propyl-1-[4-nitro-α-(o-fluorophenyl)-o-tolyl]imidazole

In the manner given in Preparation 23, 4-nitro-α-(o-fluorophenyl)-o-toluidine is reacted with triethyl orthoformate, the resulting oil is heated with 2-(1-aminopropyl)-1,3-dioxolane, and the resulting product treated with titanium tetrachloride to give 4propyl-1-[4-nitro-α-(o-fluorophenyl)-o-tolyl]imidazole In the manner given in the preceding Preparations other 1-(α-phenyl-o-tolyl)imidazoles can be obtained. Representative compounds thus obtained include:
1-(4-bromo-α-phenyl-o-tolyl)imidazole;
1-(5-bromo-α-phenyl-o-tolyl)imidazole;
5-methyl-1-[4-(trifluoromethyl)-α-(o-chlorophenyl)-o-tolyl]imidazole;
5-methyl-1-[4-fluoro-α-(o-chlorophenyl)-o-tolyl]imidazole;
4-methyl-1-(5-bromo-α-phenyl-o-tolyl)imidazole;
5-methyl-1-(5-bromo-α-phenyl-o-tolyl)imidazole;
4-methyl-1-[4-chloro-α-(o-chlorophenyl)-o-tolyl]imidazole;
4,5-dimethyl-1-(5-bromo-α-phenyl-o-tolyl)imidazole;
1-[4-chloro-α-(m-chlorophenyl)-o-tolyl]imidazole;
5-methyl-1-(4-fluoro-α-phenyl-o-tolyl)imidazole;
4-propyl-1-[α-(m-chlorophenyl)-o-tolyl]imidazole;
5-ethyl-4-propyl-1-[α-(m-chlorophenyl)-o-tolyl]imidazole;
4,5-dimethyl-1-[4-(trifluoromethyl)-α-(o-chlorophenyl)-o-tolyl]imidazole;
4,5-diethyl-1-[4-nitro-α-(o-chlorophenyl)-o-tolyl]imidazole;
5-propyl-1-(4-chloro-α-phenyl-o-tolyl)imidazole;
and the like.

Preparation 44 —
(5-Chloro-2-imidazo-1-yl)benzophenone

In a 500 ml. round bottom flask, 26.8 g. (0.100 mol) of 1-(4-chloro-α-phenyl-o-tolyl)imidazole is dissolved in 100 ml. of acetic acid. One hundred ml. of Jones reagent is added carefully and the mixture is refluxed under nitrogen for 4 hours on a steam bath. After cooling to room temperature, the mixture is poured into 4.0 liter of cold 7% aqueous sodium hydroxide solution and extracted with 2.2 liter of chloroform. The chloroform extract is washed with aqueous saturated sodium chloride, dried over anhydrous magnesium sulfate, filtered and concentrated to give a dark oil. This oil is dissolved in ethyl acetate, treated with 1.0 g. of activated charcoal, and filtered through anhydrous magnesium sulfate. Crystallization from ethyl acetate/hexane (½) affords 15.3 g. of 5-chloro-2-imidazol-1-yl)benzophenone. Recrystallization of 1.0 g. of the product from ethyl acetate affords 0.30 g. of colorless prisms, of melting point 106°–108° C.

Anal. calcd. for $C_{16}H_{11}ClN_2O$: C, 67.97; H, 3.92; N, 9.92; Cl, 12.54. Found: C, 67.54; H, 3.96; N, 10.22; Cl, 12.57.

Preparation 45 —
2′,5-Dichloro-2-(imidazol-1-yl)benzophenone

In a 500-ml. round bottom flask 30.3 g. (0.100 mol) of 1-[4-chloro-α-(o-chlorophenyl)-2-tolyl]imidazole is dissolved in 100 ml. of acetic acid. One hundred ml. of Jones reagent is added carefully and the mixture is refluxed under nitrogen for 4 hours on a steam bath. After cooling to room temperature, the mixture is poured into 4.0 l. of a cold aqueous 7% sodium hydroxide solution and extracted with 2.2 l. of chloroform. The chloroform extract is washed with an aqueous saturated sodium chloride solution, dried over anhydrous magnesium sulfate and concentrated to an oil which is crystallized from ethyl acetate to afford 2′,5-dichloro-2-(imidazol-1-yl)benzophenone of melting point 146°–148° C.

Anal. calcd. for $C_{16}H_{10}Cl_2N_2$, mw 317.17: C, 60.59; H, 3.18; N, 8.83; Cl, 22.36. Found: C, 60.96; H, 3.38; N, 8.97; Cl, 22.26.

Preparation 46 —
5-Chloro-2-(5-methylimidazol-1-yl)benzophenone

In the manner described in Preparation 44, 5-methyl-1-(4-chloro-α-phenyl-o-tolyl)imidazole in acetic acid is treated with Jones reagent and heated for 3 hours on a steam bath to give 5-chloro-2-(5-methylimidazol-1-yl)benzophenone.

Preparation 47 —
2′,5-Dichloro-2-(5-methylimidazol-1-yl)benzophenone

In the manner given in Preparation 44, 5-methyl-1-[4-chloro-α-(o-chlorophenyl)-o-tolyl]imidazole in acetic acid is heated with Jones reagent to give 2′,5-dichloro-2-(5-methylimidazol-1-yl)benzophenone.

Preparation 48 —
2′-Chloro-5-nitro-2-(imidazol-1-yl)benzophenone

In the manner given in Preparation 44, 1-[4-nitro-α-(o-chlorophenyl)-o-tolyl]imidazole in acetic acid is heated with Jones reagent to give 2′-chloro-5-nitro-2-(imidazol-1-yl)benzophenone.

Preparation 49 —
2′-Chloro-5-nitro-2-(5-methylimidazol-1-yl)benzophenone

In the manner given in Preparation 44, 5-methyl-1-[4-nitro-α-(o-chlorophenyl)-o-tolyl]imidazole in acetic acid is heated with Jones reagent to give 2′-chloro-5-nitro-2-(5-methylimidazol-1-yl)benzophenone.

Preparation 50 —
2′-Chloro-5-fluoro-2-(imidazo-1-yl)benzophenone

In the manner given in Preparation 44, 1-[4-fluoro-α-(o-chlorophenyl)-o-tolyl]imidazole in acetic acid is heated with Jones reagent to give 2′-chloro-5-fluoro-2-(imidazol-1-yl)benzophenone.

Preparation 51 —
2′-Chloro-5-fluoro-2-(5-ethylimidazol-1-yl)benzophenone

In the manner given in Preparation 44, 5-ethyl-1-[4-fluoro-α-(o-chlorophenyl)-o-tolyl]imidazole in acetic acid is heated with Jones reagent to give 2′-chloro-5-fluoro-2-(5-ethylimidazol-1-yl)benzophenone.

Preparation 52 —
5-(Trifluoromethyl)-2-(imidazol-1-yl)benzophenone

In the manner given in Preparation 44, 1-[4-(trifluoromethyl)-α-phenyl-o-tolyl]imidazole in acetic acid is heated with Jones reagent to give 5-(trifluoromethyl)-2-(imidazol-1-yl)benzophenone.

Preparation 53 — 5
-(Trifluoromethyl)-2-(5-methylimidazol-1-yl)benzophenone

In the manner given in Preparation 44, 5-methyl-1-[4-(trifluoromethyl)α-(o-chlorophenyl)-o-tolyl-]imidazole in acetic acid is heated with Jones reagent to give 5-(trifluoromethyl)-2-(5-methylimidazol-1-yl)benzophenone.

Preparation 54 —
5-Chloro-2′,6′-difluoro-2-(imidazol-1-yl)benzophenone

In the manner given in Preparation 44, 1-[4-chloro-α-(2,6-difluorophenyl)-o-tolyl]imidazole in acetic acid is heated with Jones reagent to give 5-chloro-2′,6′-difluoro-2-(imidazol-1-yl)benzophenone.

Preparation 55 —
5-Chloro-2′,6′-difluoro-2-(4-ethyl-5-methylimidazol-1-yl)benzophenone In the manner given in Preparation 44, 4-ethyl-5-methyl-1-[4-chloro-α-(2,6-difluorophenyl)-o-tolyl-]imidazole in acetic acid is heated with Jones reagent to give 5-chloro-2′,6′-difluoro-2-(4-ethyl-5-methylimidazol-1-yl)benzophenone.

Preparation 56 —
5-Nitro-2-(imidazol-1-yl)benzophenone

In the manner given in Preparation 44, 1-(4-nitro-α-phenyl-o-tolyl)imidazole in acetic acid is heated with Jones reagent to give 5-nitro-2-(imidazol-1-yl)benzophenone.

Preparation 57 —
5-Nitro-2-(5-methylimidazol-1-yl)benzophenone.

In the manner given in Preparation 44, 5-methyl-1-(4-nitro-α-phenyl-o-tolyl)imidazole in acetic acid is heated with Jones reagent to give 5-nitro-2-(5-methylimidazol-1-yl)benzophenone.

Preparation 58 —
5-Fluoro-2-(imidazol-1-yl)benzophenone

In the manner given in Preparation 44, 1-(4-fluoro-α-phenyl-o-tolyl)imidazole in acetic acid is heated with Jones reagent to give 5-fluoro-2-(imidazol-1-yl)benzophenone.

Preparation 59 —
2',5-Dichloro-2-(4-methylimidazol-1-yl)benzophenone

In the manner given in Preparation 44, 4-methyl-1-[4-chloro-α-(o-chlorophenyl)-o-tolyl]imidazole in acetic acid is heated with Jones reagent to give 2',5-dichloro-2-(4-methylimidazol-1-yl)benzophenone.

Preparation 60 —
2-(5-methylimidazol-1-yl)benzophenone

In the manner given in Preparation 44, 1-(α-phenyl-o-tolyl)imidazole in acetic acid is heated with Jones reagent to give 2-(5-methylimidazol-1-yl)benzophenone.

Preparation 61 —
2'-Chloro-2-(5-methylimidazol-1-yl)benzophenone

In the manner given in Preparation 44, 5-methyl-1-[α-(o-chlorophenyl)-o-tolyl]imidazole in acetic acid is heated with Jones reagent to give 2'-chloro-2-(5-methylimidazol-1-yl)benzophenone.

In the manner given in Preparation 44, other 2-(imidazol-1-yl)benzophenones can be produced. Representative products thus obtained include:
2'-chloro-5-(trifluoromethyl)-2-(5-methylimidazol-1-yl)benzophenone;
5-chloro-2'-fluoro-2-(imidazol-1-yl)benzophenone;
5-fluoro-2'-chloro-2-(5-methylimidazol-1-yl)benzophenone;
5-bromo-2'-chloro-2-(imidazol-1-yl)benzophenone;
2',4-dichloro-2-(4-methylimidazol-1-yl)benzophenone;
4-chloro-2-(imidazol-1-yl)benzophenone;
3-(trifluoromethyl)-2-(imidazol-1-yl)benzophenone;
3'-chloro-2-(imidazol-1-yl)benzophenone;
4',5-dichloro-2-(imidazol-1-yl)benzophenone;
5-fluoro-2-(5-methylimidazol-1-yl)benzophenone;
5-bromo-2'-chloro-2-(5-methylimidazol-1-yl)benzophenone;
5-bromo-2-(imidazol-1-yl)benzophenone;
5-chloro-2'-fluoro-2-(5-methylimidazol-1-yl)benzophenone;
5-nitro-2'-fluoro-2-(5-ethylimidazol-1-yl)benzophenone;
5-nitro-2-(5-propylimidazol-1-yl)benzophenone;
5-fluoro-2-(5-isopropylimidazol-1-yl)benzophenone;
5-(trifluoromethyl)-2-(4,5-dimethylimidazol-1-yl)benzophenone;
4-bromo-2'-chloro-2-(4,5-diethylimidazol-1-yl)benzophenone;
5-fluoro-2'-chloro-2-(4,5-dipropylimidazol-1-yl)benzophenone;
and the like.

EXAMPLE 1 —
5-Chloro-2-[2-(hydroxymethyl)-imidazol-1-yl]benzophenone

A mixture of 2.82 g. (10.0 mmol) of 5-chloro-2-(imidazol-1-yl)benzophenone in 50 ml. of a 37% aqueous formalin solution is heated to 150°C. for 6 hours in a bomb. The mixture is then poured into cold aqueous, 10% sodium hydroxide solution, and extracted 3 times with 75 ml. of chloroform. The combined chloroform extracts are dried over anhydrous sodium sulfate, filtered and chromatographed over silica gel with a solution of 3% methanol—97% chloroform. After discarding 250 ml. of forerun, 10 ml. fractions are collected. Fractions 41 to 80 contain the desired 5-chloro-2-[2-(hydroxymethyl)imidazol-1-yl]benzophenone. These fractions are combined and evaporated and the thus obtained crude product is crystallized from 20% methanol 80% ethyl acetate to give 420 mg. of 5-chloro-2-[2-(hydroxymethyl)imidazol-1-yl]benzophenone, of melting point 184°–188° C.

Anal. calcd. for $C_{17}H_{13}N_2O_2Cl$, mw 312.7: C, 65.28; H, 4.19; N, 8.96; Cl, 17.34. Found: C, 65.57; H, 4.20; N, 8.63; Cl, 11.38.

EXAMPLE 2 —
2',5-Dichloro-2-[2-(hydroxymethyl)imidazol-1-yl]benzophenone In the manner given in Example 1, 3.16 g. of 2',5-dichloro-2-(imidazol-1-yl)benzophenone is heated in a bomb with 37% aqueous formaldehyde solution to give 2',5-dichloro-2-[2-(hydroxymethyl)imidazol-1-yl]benzophenone.

EXAMPLE 3 —
5-Chloro-2-[5-methyl-2-(hydroxymethyl)imidazol-1-yl]benzophenone In the manner given in Example 1, 2.96 g. of 5-chloro-2-(5-methylimidazol-1-yl)benzophenone is heated in a bomb with paraformaldehyde in xylene to 140° C. to give 5-chloro-2-[5-methyl-2-(hydroxymethyl)imidazol-1-yl]benzophenone.

EXAMPLE 4 —
5-Chloro-2'-fluoro-2-[2-(hydroxymethyl)imidazol-1-yl]benzophenone In the manner given in Example 1, 5-chloro-2'-fluoro-2-(imidazol-1-yl)benzophenone is heated in a bomb with 37% aqueous formaldehyde solution to give 5-chloro-2'-fluoro-2-[2-(hydroxymethyl)imidazol-1-yl]benzophenone.

EXAMPLE 5 —
5-(Trifluoromethyl)-2-[2-(hydroxymethyl)-5-methylimidazol-1-yl]benzophenone In the manner given in Example 1, 5-(trifluoromethyl)-2-(5-methylimidazol-1-yl)benzophenone is heated in a bomb with paraformaldehyde in xylene to 140° C. to give 5-(trifluoromethyl)-2-[2-(hydroxymethyl)-5-methylimidazol-1-yl]benzophenone.

EXAMPLE 6 —
5-Chloro-2',6'-difluoro-2-[2-(hydroxymethyl)imidazol-1-yl]benzophenone In the manner given in Example 1, 5-chloro-2',6'-difluoro-2-(imidazol-1-yl)benzophenone is heated in a bomb to 150° C. with 37% aqueous formaldehyde solution to give 5-chloro-2',6'-difluoro-2-[2-(hydroxymethyl)imidazol-1-yl]benzophenone.

EXAMPLE 7 —
2'-Chloro-5-nitro-2-[5-methyl-2-(hydroxymethyl)imidazol-1-yl]benzophenone In the manner given in Example 1, 2'-chloro-5-nitro(5-methylimidazol-1-yl)benzophenone is heated in a bomb with paraformaldehyde in xylene to 140° C. to give 2'-chloro-5-nitro-2-[5-methyl-2-(hydroxymethyl)imidazol-1-yl]benzophenone.

EXAMPLE 8 —
2'-Chloro-5-(trifluoromethyl)-2-[2-(hydroxymethyl)-5-methylimidazol-1-yl]benzophenone In the manner given in Example 1, 2'-chloro-5-(trifluoromethyl)-2-(5-methylimidazol-1-yl)benzophenone is heated in a bomb with 37% aqueous formaldehyde solution to give 2'-chloro-5-(trifluoromethyl)-2-[2-(hydroxymethyl)-5-methylimidazol-1-yl]benzophenone.

EXAMPLE 9 —
2'-Chloro-2-[2-(hydroxymethyl)imidazol-1-yl]benzophenone

In the manner given in Example 1, 2'-chloro-2-imidazol-1-yl)benzophenone is heated in a bomb with paraformaldehyde in xylene to 140° C. to give 2-chloro-2-[2-(hydroxymethyl)imidazol-1-yl]-benzophenone.

EXAMPLE 10 —
5-Bromo-2-[2-(hydroxymethyl)imidazol-1-yl]benzophenone

In the manner given in Example 1, 5-bromo-2-(imidazol-1-yl)benzophenone is heated in a bomb with 37% aqueous formaldehyde solution to give 5-bromo-2-[2-(hydroxymethyl)imidazol-1-yl]benzophenone.

EXAMPLE 11 —
2',5-Dichloro-2-[2-(hydroxymethyl)-5-methylimidazol-1-yl]benzophenone In the manner given in Example 1, 2',5-dichloro-2-(5-methylimidazol-1-yl)benzophenone is heated in a bomb to 150° C. with 37% aqueous formaldehyde solution to give 2',5-dichloro-2-[2-(hydroxymethyl)-5-methylimidazol-1-yl]benzophenone.

EXAMPLE 12 —
2'-Chloro-5-nitro-2-[2-(hydroxymethyl)imidazol-1-yl]benzophenone In the manner given in Example 1, 2'-chloro-5-nitro-2-(imidazol-1-yl)benzophenone is heated in a bomb with paraformaldehyde in xylene to 140° C. to give 2'-chloro-5-nitro-2-[2-(hydroxymethyl)imidazol-1-yl]benzophenone.

EXAMPLE 13 —
2'-Chloro-5-fluoro-2-[2-(hydroxymethyl)imidazol-1-yl]benzophenone In the manner given in Example 1, 2'-chloro-5-fluoro-2-(imidazol-1-yl)benzophenone is heated in a bomb to 150° C. with 37% aqueous formaldehyde solution to give 2'-chloro-5-fluoro-2-[2-(hydroxymethylimidazol-1-yl]benzophenone.

EXAMPLE 14 —
5-Nitro-2-[2-(hydroxymethyl)imidazol-1-yl]benzophenone

In the manner given in Example 1, 5-nitro-2-(imidazol-1-yl)benzophenone is heated in a bomb with paraformaldehyde in xylene to 140° C. to give 5-nitro-2-[2-(hydroxymethyl)imidazol-1-yl]benzophenone.

EXAMPLE 15 —
5-Fluoro-2-[2-(hydroxymethyl)imidazol-1-yl]benzophenone

In the manner given in Example 1, 5-fluoro-2-(imidazol-1-yl)benzophenone is heated in a bomb to 150° C. with 37% aqueous formaldehyde solution to give 5-fluoro-2-[2-(hydroxymethyl)imidazol-1-yl]benzophenone.

EXAMPLE 16 —
5-(Trifluoromethyl)-2-[2-(hydroxymethyl)imidazol-1-yl]benzophenone In the manner given in Example 1, 5-(trifluoromethyl)-2-(imidazol-1-yl)benzophenone is heated in a bomb with paraformaldehyde in xylene to 140° C. to give 5-(trifluoromethyl)-2-[2-(hydroxymethyl)imidazol-1-yl]benzophenone.

In the manner given in the preceding Examples, other 2-[2-(hydroxymethyl)imidazol-1-yl]benzophenones of formula II can be produced. Representative compounds thus obtained include:

2',5-dichloro-2-[2-(hydroxymethyl)-4-methylimidazol-1-yl]benzophenone;
2',5-dichloro-2-[2-(hydroxymethyl)-5-ethylimidazol-1-yl]benzophenone;
2',5-dichloro-2[2-(hydroxymethyl)-5-propylimidazol-1-yl]benzophenone;
4-chloro-2-[2-(hydroxymethyl)-5-methylimidazol-1-yl]benzophenone;
3-chloro-2-[2-(hydroxymethyl)-5-methylimidazol-1-yl]benzophenone;
6-chloro-2-[2-(hydroxymethyl)-5-methylimidazol-1-yl]benzophenone;
5-bromo-2'-chloro-2-[2-(hydroxymethyl)-5-methylimidazol-1-yl]benzophenone;
5-(trifluoromethyl)-2-[2-(hydroxymethyl)-4-methylimidazol-1-yl]benzophenone;
5-(trifluoromethyl)-2'-chloro-2-[2-(hydroxymethyl)-4,5-dimethylimidazol-1-yl]benzophenone;
5-nitro-2-[2-(hydroxymethyl)-4-methyl-5-ethylimidazol-1-yl]benzophenone;
6-nitro-3'-chloro-2-[2-(hydroxymethyl)-4-methylimidazol-1-yl]benzophenone;
3-nitro-4'-chloro-2-[2-(hydroxymethyl)-4,5-diethylimidazol-1-yl]benzophenone;
5-chloro-2',6'-difluoro-2-[2-(hydroxymethyl)-4,5-dipropylimidazol-1-yl]benzophenone;
5-chloro-2',6'-difluoro-2-[2-(hydroxymethyl)-4-propyl-5-methylimidazol-1-yl]benzophenone;
2'-chloro-2-[2-(hydroxymethyl)-5-methylimidazol-1-yl]benzophenone;
5-bromo-2-[2-(hydroxymethyl)-4-ethylimidazol-1-yl]benzophenone;
4-bromo-2-[2-(hydroxymethyl)-5-methylimidazol-1-yl]benzophenone;
3-fluoro-3'-chloro-2-[2-(hydroxymethyl)-4-ethylimidazol-1-yl]benzophenone;
6-fluoro-2'-chloro-2-[2-(hydroxymethyl)-5-isopropylimidazol-1-yl]benzophenone;

5-fluoro-4'-chloro-2-[2-(hydroxymethyl)-5-methylimidazol-1-yl]benzophenone; and the like.

EXAMPLE 17 —
5-Chloro-2-[2-(phthalimidomethyl)imidazol-1-yl]benzophenone

A mixture of 6.254 g. (20.0 mmol) of 5-chloro-2-[2-(hydroxymethyl)imidazol-1-yl]benzophenone, 3.24 g. (22.0 mmol) of phthalimide and 5.76 g. (22.0 mmol) of triphenylphosphine suspended in 200 ml. of freshly distilled tetrahydrofuran and cooled for one-half hour in an ice bath is treated dropwise with 3.83 g. (22.0 mmol) of diethyl azodicarboxylate over three-fourths hour. By the end of the addition, all of the suspended solid has gone into solution. After overnight stirring (with concomitant warming to room temperature) the white powder which settled from the solution is filtered to give 3.56 g. of 5-chloro-2[2-(phthalimidomethylimidazol-1-yl]benzophenone of melting point 194°–198° C. The analytical sample has a melting point 194°–197° C.

Anal. calcd. for $C_{25}H_{16}ClN_3O_3$, mw 441.86: C, 67.95; H, 3.65; N, 9.51; Cl, 8.02. Found: C, 68.06; H, 3.76; N, 9.65; Cl, 8.00.

EXAMPLE 18 —
2',5-Dichloro-2-[2-(phthalimidomethyl)imidazol-1-yl]benzophenone In the manner given in Example 17, 3.47 g. (20.0 mmol) of 2',5-dichloro-2-[2-(hydroxymethyl)imidazol-1-yl]benzophenone is treated with 3.24 g. (22.0 mmol) of phthalimide and 5.76 g. (22.0 mmol) of triphenylphosphine suspended in 200 ml. of cold (0°–5°) tetrahydrofuran and finally with 3.83 g. (22.0 mmol) of diethyl azodicarboxylate, added slowly over three-fourths hour. After overnight stirring, the resulting solid is filtered and crystallized to afford 2',5-dichloro-2-[2-(phthalimidomethyl)imidazol-1-yl]benzophenone.

EXAMPLE 19 —
5-Chloro-2-[5-methyl-2-(phthalimidomethyl)imidazol-1-yl]benzophenone In the manner given in Example 17, 5-chloro-2-[5-methyl-2-(hydroxymethyl)imidazol-1-yl]benzophenone is treated with phthalimide and triphenylphosphine and finally with diethyl azodicarboxylate to give 5-chloro-2-[5-methyl-2-(phthalimidomethyl)imidazol-1-yl]benzophenone.

EXAMPLE 20 —
5-Fluoro-2-[2-(phthalimidomethyl)imidazol-1-yl]benzophenone

In the manner given in Example 17, 5-fluoro-2-[2-(hydroxymethyl)imidazol-1-yl]benzophenone is treated with phthalimide and triphenylphosphine and finally with diethyl azodicarboxylate to give 5-fluoro-2-[2-(phthalimidomethyl)imidazol-1-yl]benzophenone.

EXAMPLE 21 —
2',5-Dichloro-2-[4-methyl-2-(phthalimidomethyl)imidazol-1-yl]benzophenone In the manner given in Example 17, 2',5-dichloro-[2-(hydroxymethyl)-4-methylimidazol-1-yl]benzophenone is treated with phthalimide and triphenylphosphine and finally with diethyl azocarboxylate to give 2',5-dichloro-2-[4-methyl-2-(phthalimidomethyl)imidazol-1-yl]benzophenone.

EXAMPLE 22 —
5-Chloro-2'-fluoro-2-[2-(phthalimidomethyl)imidazol-1-yl]benzophenone In the manner given in Example 17, 5-chloro-2'-fluoro-2-[2-(hydroxymethyl)imidazol-1-yl]benzophenone is treated with phthalimide and triphenylphosphine and finally with diethyl azodicarboxylate to give 5-chloro-2'-fluoro-2-[2-(phthalimidomethyl)imidazol-1-yl]benzophenone.

EXAMPLE 23 —
5-(Trifluoromethyl)-2-[2-(phthalimidomethyl)imidazol-1-yl]benzophenone In the manner given in Example 17, 5-(trifluoromethyl)-2-[2-(hydroxymethyl)imidazol-1-yl]benzophenone is treated with phthalimide and triphenylphosphine and finally with diethyl azocarboxylate to give 5-(trifluoromethyl)-2-[2-(phthalimidomethyl)imidazol-1-yl]benzophenone.

EXAMPLE 24 —
5-Chloro-2',6'-difluoro-2-[2-phthalimidomethyl)imidazol-1-yl]benzophenone In the manner given in Example 17, 5-chloro-2',6'-difluoro-2-[2-(hydroxymethyl)imidazol-1-yl]benzophenone is treated with phthalimide and triphenylphosphine and finally with diethyl azodicarboxylate to give 5-chloro-2',6'-difluoro-2-[2-(phthalimidomethyl)imidazol-1-yl]benzophenone.

EXAMPLE 25 —
2'-Chloro-5-nitro-2-[5-methyl-2-(phthalimidomethyl)imidazol-1-yl]benzophenone In the manner given in Example 17, 2'-chloro-5-nitro-2-[5-methyl-2-(hydroxymethyl)imidazol-1-yl]benzophenone is treated with phthalimide and triphenylphosphine and finally with diethyl azodicarboxylate to give 2'-chloro-5-nitro-2-[5-methyl-2-(phthalimidomethyl)imidazol-1-yl]benzophenone.

EXAMPLE 26 —
2'-Chloro-5-(trifluoromethyl)-2-[5-methyl-2-(phthalimidomethyl)imidazol-1-yl]benzophenone In the manner given in Example 17, 2'-chloro-2-[5-(trifluoromethyl)-2-[5-methyl-2-(hydroxymethyl)imidazol-1-yl]benzophenone is treated with phthalimide and triphenylphosphine and finally with diethyl azodicarboxylate to give 2'-chloro-5'-(trifluoromethyl)-2-[5-methyl-2-(phthalimidomethyl)imidazol-1-yl]benzophenone.

EXAMPLE 27 —
2'-Chloro-2-[2-(phthalimidomethyl)imidazol-1-yl]benzophenone

In the manner given in Example 17, 2'-chloro-2-[2-(hydroxymethyl)imidazol-1-yl]benzophenone is treated with phthalimide and triphenylphosphine and finally with diethyl azodicarboxylate to give 2'-chloro-2-[2-(phthalimidomethyl)imidazol-1-yl]benzophenone.

EXAMPLE 28 —
5-Bromo-2-[2-(phthalimidomethyl)imidazol-1-yl]benzophenone

In the manner given in Example 17, 5-bromo-2-[2-(hydroxymethyl)imidazol-1-yl]benzophenone is treated with phthalimide and triphenylphosphine and finally with diethyl azodicarboxylate to give 5-bromo-2-[2-(phthalimidomethyl)imidazol-1-yl]benzophenone.

EXAMPLE 29 —
2',5-Dichloro-2-[5-methyl-2-(phthalimidomethyl)imidazol-1-yl]benzophenone In the manner given in Example 17, 2',5-dichloro-2-[5-methyl-2-(hydroxymethyl)imidazol-1-yl]benzophenone is treated with phthalimide and triphenylphosphine and finally with diethyl azodicarboxylate to give 2',5'-dichloro-2-[5-methyl-2-(phthalimidomethyl)imidazol-1-yl]benzophenone.

EXAMPLE 30 —
2'-Chloro-5-nitro-2-[2-(phthalimidomethyl)imidazol-1-yl]benzophenone In the manner given in Example 17, 2'-chloro-5-nitro-2-[2-(hydroxymethyl)imidazol-1-yl]benzophenone is treated with phthalimide and triphenylphosphine and finally with diethyl azodicarboxylate to give 2'-chloro-5-nitro-2-[2-phthalimidomethyl)imidazol-1-yl]benzophenone.

EXAMPLE 31 —
2'-Chloro-5-fluoro-2-[2-(phthalimidomethyl)imidazol-1-yl]benzophenone In the manner given in Example 17, 2'-chloro-5-fluoro-2-[2-(hydroxymethyl)imidazol-1-yl]benzophenone is treated with phthalimide and triphenylphosphine and finally with diethyl azodicarboxylate to give 2'-chloro-5-fluoro-2-[2-(phthalimidomethyl)imidazol-1-yl]benzophenone.

EXAMPLE 32 —
5-Nitro-2-[2-(phthalimidomethyl)imidazol-1-yl]benzophenone

In the manner given in Example 17, 5-nitro-2-[2-(hydroxymethyl)imidazol-1-yl]benzophenone is treated with phthalimide and triphenylphosphine and finally with diethyl azodicarboxylate to give 5-nitro-2-[2-(phthalimidomethyl)imidazol-1-yl]benzophenone.

In the manner given in the preceding Examples 17 through 32, other 2-[(2-phthalimidomethyl)imidazol-1-yl]benzophenones of formula III can be produced. Representative compounds, thus obtained, include:

2',5-dichloro-2-[4-methyl-2-(phthalimidomethyl)imidazol-1-yl]benzophenone;
2',5-dichloro-2-[5-ethyl-2-(phthalimidomethyl)imidazol-1-yl]benzophenone;
2',5-dichloro-2-[5-propyl-2-(phthalimidomethyl)imidazol-1-yl]benzophenone;
4-chloro-2-[5-methyl-2-(phthalimidomethyl)imidazol-1-yl]benzophenone;
3-chloro-2-[5-methyl-2-(phthalimidomethyl)imidazol-1-yl]benzophenone;
6-chloro-2-[5-methyl-2-(phthalimidomethyl)imidazol-1-yl]benzophenone;
5-bromo-2'-chloro-2-[5-methyl-2-(phthalimidomethyl)imidazol-1-yl]benzophenone;
5-(trifluoromethyl)-2-[4-methyl-2-(phthalimidomethyl)imidazol-1-yl]benzophenone;
5-(trifluoromethyl)-2'-chloro-2-[4,5-dimethyl-2-(phthalimidomethyl)imidazol-1-yl]benzophenone;
5-nitro-2-[4-methyl-5-ethyl-2-(phthalimidomethyl)imidazol-1-yl]benzophenone;
6-nitro-3'-chloro-2-[4-methyl-2-(phthalimidomethyl)imidazol-1-yl]benzophenone;
3-nitro-4'-chloro-2-[4,5-diethyl-2-(phthalimidomethyl)imidazol-1-yl]benzophenone;
5-chloro-2',6'-difluoro-2-[4,5-dipropyl-2-(phthalimidomethyl)imidazol-1-yl]benzophenone;
5-chloro-2',6'-difluoro-2-[4-propyl-5-methyl-2-(phthalimidomethyl)imidazol-1-yl]benzophenone;
2'-chloro-2-[5-methyl-2-(phthalimidomethyl)imidazol-1-yl]benzophenone;
5-bromo-2-[4-ethyl-2-(phthalimidomethyl)imidazol-1-yl]benzophenone;
4-bromo-2-[5-methyl-2-(phthalimidomethyl)imidazol-1-yl]benzophenone;
3-fluoro-3'-chloro-2-[4-ethyl-2-(phthalimidomethyl)imidazol-1-yl]benzophenone;
6-fluoro-2'-chloro-2-[5-isopropyl-2-(phthalimidomethyl)imidazol-1-yl]benzophenone;
5-fluoro-4'-chloro-2-[5-methyl-2-(phthalimidomethyl)imidazol-1-yl]benzophenone;
5-(trifluoromethyl)-2-[5-methyl-2-(phthalimidomethyl)imidazol-1-yl]benzophenone;
and the like.

EXAMPLE 33 —
8-Chloro-6-phenyl-4H-imidazo[1,2-a][1,4]benzodiazepine

5-Chloro-2-[2-(phthalimidomethyl)imidazol-1-yl]benzophenone (0.883 g., 2.00 mmol) is suspended in 12 ml. of absolute ethanol, treated with hydrazine and heated to 72°–74° C. Within 10 minutes all of the solid dissolves. After 2 hours the reaction is stopped and white solid is removed by filtration. The mother liquor is concentrated in vacuo to an oil which is crystallized from ethyl acetate-hexane-mixtures to give 8-chloro-6-phenyl-4H-imidazo[1,2-a][1,4]benzodiazepine of melting point 143°–148° C.

Anal. calcd. for $C_{17}H_{12}ClN_3$: C, 69.50; H, 4.12; N, 14.31; Cl, 12.07. Found: C, 69.32; H, 4.04; N, 14.51; Cl, 12.08.

EXAMPLE 34 —
8-Chloro-6-(o-chlorophenyl)-4H-imidazo[1,2-a][1,4benzodiazepine In the manner given in Example 33, 2',5-dichloro-2-[2-(phthalimidomethyl)imidazol-1-yl]benzophenone (4.76 g., 10.0 mmol) is dissolved in 60 ml. of ethanol, treated with 1.00 ml. of hydrazine hydrate and heated to 73° C. for 2 hours. After filtration of the reaction mixture, the mother liquids are concentrated and the residue is recrystallized from ethyl acetate/hexane mixtures to give 8-chloro-6-(o-chlorophenyl)-4H-imidazo[1,2-a][1,4]benzodiazepine of melting point 178°–180° C.

Anal. calcd. for $C_{17}H_{11}Cl_2N_3$: C, 62.21; H, 3.38; N, 12.81; Cl, 21.60. Found: C, 61.98; H, 3.27; N, 13.08; Cl, 21.72.

EXAMPLE 35 —
1-Methyl-8-chloro-6-phenyl-4H-imidazo[1,2-a][1,4]benzodiazepine

In the manner given in Example 33, 5-chloro-2-[1-(phthalimidomethyl)-5-methylimidazol-1-yl]benzophenone is treated with hydrazine in ethanol at 73°C. to give 1-methyl-8-chloro-6-phenyl-4H-imidazo[1,2-a][1,4]benzodiazepine of melting point 190°–191° C.

Anal. calcd. for $C_{18}H_{14}ClN_3$: C, 70.24; H, 4.58; N, 13.66; Cl, 11.52. Found: C, 70.57; H, 4.52; N, 13.64; Cl, 11.61.

EXAMPLE 36 —
8-Fluoro-6-phenyl-4H-imidazo[1,2-a][1,4]benzodiazepine

In the manner given in Example 33, 5-fluoro-2-[2-(phthalimidomethyl)imidazol-1-yl]benzophenone in ethanol is heated with hydrazine to give 8-fluoro-6-phenyl-4H-imidazo[1,2-a][1,4]benzodiazepine.

EXAMPLE 37 —
8-Chloro-6-(o-chlorophenyl)-2-methyl-4H-imidazo[1,2-a][1,4]benzodiazepine In the manner given in Example 25, 2',5-dichloro-2-[4-methyl-2-(phthalimidomethyl)imidazol-1-yl]benzophenone in ethanol is heated with hydrazine to give 8-chloro-6-(o-chlorophenyl)-2-methyl-4H-imidazo[1,2-a][1,4]benzodiazepine.

EXAMPLE 38 —
8-Chloro-6-(o-fluorophenyl)-4H-imidazo[1,2-a][1,4]benzodiazepine In the manner given in Example 33, 5-chloro-2'-fluoro-2-[2-(phthalimidomethyl)imidazol-1-yl]benzophenone in ethanol is heated with hydrazine to give 8-chloro-6-(o-fluorophenyl)-4H-imidazo[1,2-a][1,4]benzodiazepine.

EXAMPLE 39 —
8-Nitro-6-(o-chlorophenyl)-1-methyl-4H-imidazo[1,2-a][1,4]benzodiazepine In the manner given in Example 25, 2'-chloro-5-nitro-2-[5-methyl-2-(phthalimidomethyl)imidazol-1-yl]benzophenone in ethanol is heated with hydrazine to give 8-nitro-6-(o-chlorophenyl)-1-methyl-4H-imidazo[1,2-a][1,4]benzodiazepine

EXAMPLE 40 —
8-Chloro-6-(2,6-difluorophenyl)-4H-imidazo[1,2-a][1,4]benzodiazepine In the manner given in Example 33, 5-chloro-2',6'-difluoro-2-[2-(phthalimidomethyl)imidazol-1-yl]benzophenone in ethanol is heated with hydrazine to give 8-chloro-6-(2,6-difluorophenyl)-4H-imidazo[1,2-a][1,4]benzodiazepine.

EXAMPLE 41 —
6-(o-chlorophenyl)4H-imidazo[1,2-a][1,4]benzodiazepine.

In the manner given in Example 33, 2'-chloro-2-[2-(phthalimidomethyl)imidazol-1-yl]benzophenone in ethanol is heated with hydrazine to give 6-(o-chlorophenyl)-4H-imidazo[1,2-a][1,4]benzodiazepine.

EXAMPLE 42 —
8-Bromo-6-phenyl-4H-imidazo[1,2-a][1,4]benzodiazepine

In the manner given in Example 33, 5-bromo-2-[2-(phthalimidomethyl)imidazol-1-yl]benzophenone in ethanol is heated with hydrazine to give 8-bromo-6-phenyl-4H-imidazo[1,2-a][1,4]benzodiazepine.

In the same manner shown in Example 33 through 42, other 2-[(2-phthalimidomethyl)imidazo-1-yl]benzophenones of formula IV can be converted to the corresponding known 6-phenyl-4H-imidazo[1,2-a][1,4]benzodiazepines IV, which are useful tranquilizing, sedative, and musclerelaxing agents.

I claim:

1. A compound of the formula II:

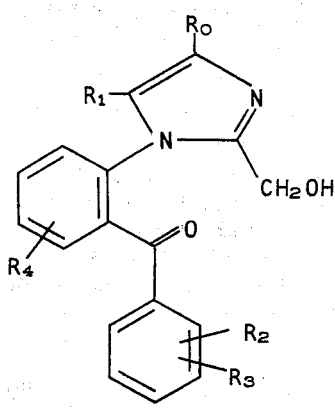

II wherein $R_0$ and $R_1$ are hydrogen or alkyl of 1 to 3 carbon atoms, inclusive; wherein $R_2$ is hydrogen, chloro, fluoro, or trifluoromethyl; wherein $R_3$ is hydrogen, or fluoro with the proviso that $R_3$ is not fluoro, if $R_2$ is chloro or trifluoromethyl; and wherein $R_4$ is hydrogen, fluoro, chloro, bromo, nitro, or trifluoromethyl, 2. A compound according to claim 1 of the formula IIA:

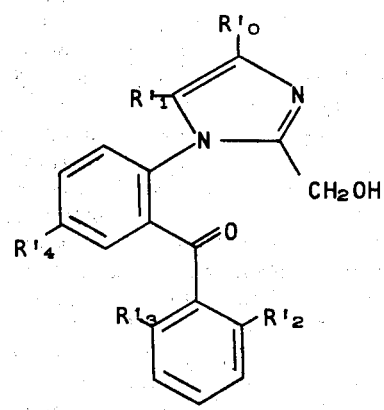

IIA wherein $R'_0$ and $R'_1$ are hydrogen or methyl; wherein $R'_2$ is hydrogen, chloro, or fluoro; wherein $R'_3$ is hydrogen or fluoro with the proviso that $R'_3$ is not fluoro if $R'_2$ is chloro; wherein $R'_4$ is hydrogen, chloro, fluoro, or trifluoromethyl.

3. A compound according to claim 1 of the formula IIB:

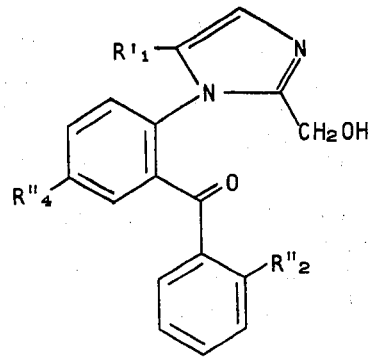

wherein R'₁ is hydrogen or methyl; wherein R''₂ is hydrogen or chloro; wherein R''₄ is hydrogen, chloro, or fluoro.

4. A compound according to claim 3, wherein R'₁ and R''₂ are hydrogen; R''₄ is chloro, and the compound is therefore 5-chloro-2-[2-(hydroxymethyl)imidazol-1-yl]benzophenone.

5. A compound according to claim 3, wherein R'₁ is hydrogen; wherein R''₂ and R''₄ are chloro and the compound is therefore 2',5-dichloro-2-[2-(hydroxymethyl)imidazol-1-yl]benzophenone.

6. A compound according to claim 3, wherein R'₁ is methyl, R''₂ is hydrogen, R''₄ is chloro and the compound is therefore 5-chloro-2-[2-(hydroxymethyl)-5-methylimidazol-1-yl]benzophenone.

7. A compound according to claim 3, wherein R'₁ and R''₂ are hydrogen, R''₄ is fluoro and the compound is therefore 5-fluoro-2-[2-(hydroxymethyl)imidazol-1-yl]benzophenone.

8. A compound according to claim 2, wherein R'₀ is methyl, R'₁ is hydrogen, R'₂ and R'₄ are chloro and the compound is therefore 2',5-dichloro-2-[2-(hydroxymethyl)-4-methylimidazol-1-yl]benzophenone.

9. A compound according to claim 2, wherein R'₁ and R'₀ are hydrogen, R'₂ is fluoro, R'₄ is chloro, and the compound is therefore 2'-fluoro-5-chloro-2-[2-(hydroxymethyl)imidazol-1-yl]benzophenone.

10. A compound according to claim 2, wherein R'₀ and R'₂ are hydrogen; R'₁ is methyl; R'₄ is trifluoromethyl and the compound is therefore 5-(trifluoromethyl)-2-[2(hydroxymethyl)-5-methylimidazol-1-yl]benzophenone.

11. A compound according to claim 1, wherein R₀, R₁, R₂, and R₃ are hydrogen, R₄ is nitro and the compound is therefore 5-nitro-2-[2-(hydroxymethyl)imidazol-1-yl]benzophenone.

12. A compound of the formula III:

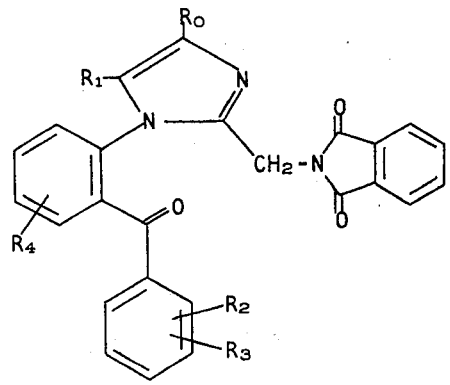

wherein R₀ and R₁ are hydrogen or alkyl of 1 to 3 carbon atoms, inclusive; wherein R₂ is hydrogen, chloro, fluoro, or trifluoromethyl; wherein R₃ is hydrogen or fluoro with the proviso that R₃ is not fluoro, if R₂ is chloro or trifluoromethyl; and wherein R₄ is hydrogen, chloro, fluoro, bromo, nitro, or trifluoromethyl.

13. A compound according to claim 12, of the formula IIIA:

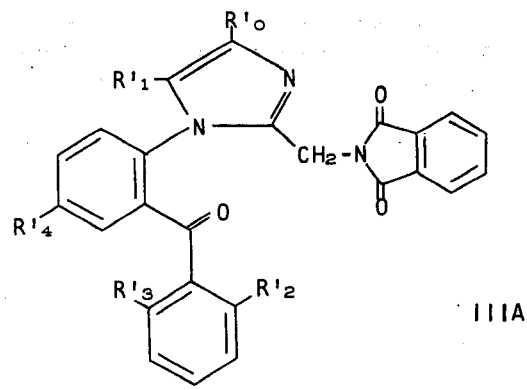

wherein R'₀ and R'₁ are hydrogen or methyl; wherein R'₂ is hydrogen, chloro, or fluoro; wherein R'₃ is hydrogen, or fluoro with the proviso that R'₃ is not fluoro if R'₂ is chloro; wherein R₄ is hydrogen, chloro, fluoro or trifluoromethyl.

14. A compound according to claim 12 of the formula IIIB:

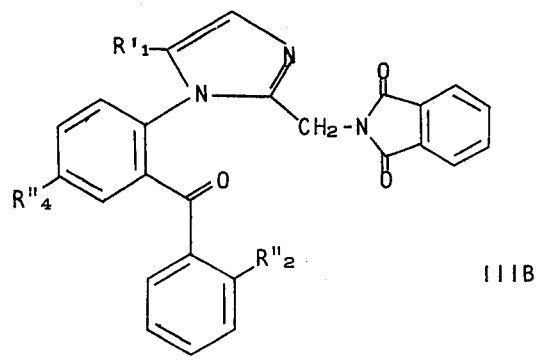

wherein R'₁ is hydrogen or methyl; wherein R''₂ is hydrogen or chloro; wherein R''₄ is hydrogen, chloro, or fluoro.

15. A compound according to claim 14 wherein R'₁ and R''₂ are hydrogen, R''₄ is chloro and the compound is therefore 5-chloro-2-[2-(phthalimidomethyl)imidazol-1-yl]benzophenone.

16. A compound according to claim 14, wherein R'₁ is hydrogen, wherein R''₂ and R''₄ are chloro and the compound is therefore 2',5-dichloro-2-[2-(phthalimidomethyl)imidazol-1-yl]benzophenone.

17. A compound according to claim 14, wherein $R'_1$ is methyl, $R''_2$ is hydrogen, $R''_4$ is chloro and the compound is therefore 5-chloro-2-[2-(phthalimidomethyl)-5-methylimidazol-1-yl]benzophenone.

18. A compound according to claim 14, wherein $R'_1$ and $R''_2$ are hydrogen, $R''_4$ is fluoro and the compound is therefore 5-fluoro-2-[2-(phthalimidomethyl)imidazol-1-yl]benzophenone.

19. A compound according to claim 13, wherein $R'_0$ is methyl, $R'_1$ is hydrogen, $R'_2$ and $R'_4$ are chloro and the compound is therefore 2',5-dichloro-2-[2-(phthalimidomethyl)-4-methylimidazol-1-yl]benzophenone.

20. A compound according to claim 13, wherein $R'_1$ and $R'_0$ are hydrogen, $R''_2$ is fluoro, $R'_4$ is chloro and the compound is therefore 2'-fluoro-5-chloro-2-[2-(phthalimidomethyl)-4-imidazol-1-yl]benzophenone.

21. A compound according to claim 13, wherein $R_0'$ and $R'_2$ are hydrogen, $R'_1$ is methyl, $R'_4$ is trifluoromethyl and the compound is therefore 5-(trifluoromethyl)-1-[2-(phthalimidomethyl)-5-methylimidazol-1-yl]benzophenone.

22. A compound according to claim 12, wherein $R_0$, $R_1$, $R_2$, and $R_3$ are hydrogen, $R_4$ is nitro and the compound is therefore 5-nitro-2-[2-(phthalimidomethyl)imidazol-1-yl]benzophenone.

* * * * *